US009226826B2

(12) United States Patent
Rust

(10) Patent No.: US 9,226,826 B2
(45) Date of Patent: Jan. 5, 2016

(54) TRANSCATHETER VALVE STRUCTURE AND METHODS FOR VALVE DELIVERY

(75) Inventor: Matthew J. Rust, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 590 days.

(21) Appl. No.: 12/711,289

(22) Filed: Feb. 24, 2010

(65) Prior Publication Data

US 2011/0208283 A1 Aug. 25, 2011

(51) Int. Cl.
*A61F 2/24* (2006.01)

(52) U.S. Cl.
CPC ............ *A61F 2/2436* (2013.01); *A61F 2/2418* (2013.01); *A61F 2/2409* (2013.01); *A61F 2/2412* (2013.01); *A61F 2220/0075* (2013.01); *A61F 2230/008* (2013.01); *A61F 2230/0054* (2013.01)

(58) Field of Classification Search
CPC ............ A61F 2/915; A61F 2/07; A61F 2/89; A61F 2/2418; A61F 2/2475
USPC .............................. 623/1.11, 1.24, 2.17–2.18
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |

(Continued)

FOREIGN PATENT DOCUMENTS

CN 2007-100074433 1/2007
DE 3640745 6/1987

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Thomas J Sweet
*Assistant Examiner* — Seema Mathew

(57) ABSTRACT

A valved stent including a stent structure having a generally tubular body portion with an interior area, a first end, a second end, and a longitudinal axis; a valve structure including a plurality of leaflets and positioned within the interior area of the stent structure; and an invertible structure extending from one of the first and second ends of the stent structure. The invertible structure can be rotatable relative to the end of the stent structure from which it extends.

11 Claims, 4 Drawing Sheets

(56) References Cited

U.S. PATENT DOCUMENTS

| | | |
|---|---|---|
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,556,996 A * | 12/1985 | Wallace ............... A61F 2/2403 623/2.2 |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,777 A * | 2/1999 | Lam ..................... A61F 2/90 606/194 |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |

(56) References Cited

U.S. PATENT DOCUMENTS

| | | |
|---|---|---|
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,780,726 B2 | 8/2010 | Seguin |
| 7,806,919 B2 | 10/2010 | Bloom et al. |
| 8,163,004 B2 * | 4/2012 | Amplatz ............ A61F 2/07 623/1.12 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |

(56) References Cited

U.S. PATENT DOCUMENTS

| | | |
|---|---|---|
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1* | 1/2003 | Bailey et al. ............... 623/1.13 |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093058 A1* | 5/2004 | Cottone ............... A61F 2/07 623/1.11 |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254627 A1* | 12/2004 | Thompson ............... A61F 2/91 623/1.11 |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222672 A1* | 10/2005 | Shmulewitz ............... A61F 2/88 623/1.15 |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |

(56) References Cited

U.S. PATENT DOCUMENTS

| | | | |
|---|---|---|---|
| 2006/0058775 | A1 | 3/2006 | Stevens et al. |
| 2006/0089711 | A1 | 4/2006 | Dolan |
| 2006/0100685 | A1 | 5/2006 | Seguin et al. |
| 2006/0116757 | A1 | 6/2006 | Lashinski et al. |
| 2006/0135964 | A1 | 6/2006 | Vesely |
| 2006/0142848 | A1 | 6/2006 | Gabbay |
| 2006/0167474 | A1 | 7/2006 | Bloom et al. |
| 2006/0178740 | A1 | 8/2006 | Stacchino et al. |
| 2006/0195134 | A1 | 8/2006 | Crittenden |
| 2006/0206192 | A1 | 9/2006 | Tower et al. |
| 2006/0206202 | A1 | 9/2006 | Bonhoefer et al. |
| 2006/0212111 | A1 | 9/2006 | Case et al. |
| 2006/0247763 | A1 | 11/2006 | Slater |
| 2006/0259134 | A1 | 11/2006 | Schwammenthal et al. |
| 2006/0259136 | A1 | 11/2006 | Nguyen et al. |
| 2006/0259137 | A1 | 11/2006 | Artof et al. |
| 2006/0265056 | A1 | 11/2006 | Nguyen et al. |
| 2006/0271166 | A1 | 11/2006 | Thill et al. |
| 2006/0271175 | A1 | 11/2006 | Woolfson et al. |
| 2006/0276874 | A1 | 12/2006 | Wilson et al. |
| 2006/0276882 | A1 | 12/2006 | Case et al. |
| 2006/0282161 | A1 | 12/2006 | Huynh et al. |
| 2007/0005129 | A1 | 1/2007 | Damm et al. |
| 2007/0005131 | A1 | 1/2007 | Taylor |
| 2007/0010878 | A1 | 1/2007 | Raffiee et al. |
| 2007/0016286 | A1 | 1/2007 | Herrmann et al. |
| 2007/0027518 | A1 | 2/2007 | Case et al. |
| 2007/0027533 | A1 | 2/2007 | Douk |
| 2007/0038295 | A1 | 2/2007 | Case et al. |
| 2007/0043431 | A1* | 2/2007 | Melsheimer ......... A61F 2/2418 623/1.24 |
| 2007/0043435 | A1 | 2/2007 | Seguin et al. |
| 2007/0051377 | A1 | 3/2007 | Douk et al. |
| 2007/0073392 | A1 | 3/2007 | Heyninck-Janitz |
| 2007/0078509 | A1 | 4/2007 | Lotfy et al. |
| 2007/0078510 | A1 | 4/2007 | Ryan |
| 2007/0088431 | A1 | 4/2007 | Bourang et al. |
| 2007/0093869 | A1 | 4/2007 | Bloom et al. |
| 2007/0093887 | A1* | 4/2007 | Case ......... A61F 2/2418 623/1.24 |
| 2007/0100439 | A1 | 5/2007 | Cangialosi |
| 2007/0100440 | A1 | 5/2007 | Figulla |
| 2007/0100449 | A1 | 5/2007 | O'Neil et al. |
| 2007/0112415 | A1 | 5/2007 | Bartlett |
| 2007/0112422 | A1 | 5/2007 | Dehdashtian |
| 2007/0162102 | A1 | 7/2007 | Ryan et al. |
| 2007/0162113 | A1 | 7/2007 | Sharkawy et al. |
| 2007/0185513 | A1 | 8/2007 | Woolfson et al. |
| 2007/0203391 | A1 | 8/2007 | Bloom et al. |
| 2007/0225681 | A1 | 9/2007 | House |
| 2007/0232898 | A1 | 10/2007 | Huynh et al. |
| 2007/0233228 | A1 | 10/2007 | Eberhardt et al. |
| 2007/0233237 | A1 | 10/2007 | Krivoruchko |
| 2007/0233238 | A1 | 10/2007 | Huynh et al. |
| 2007/0238979 | A1 | 10/2007 | Huynh et al. |
| 2007/0239254 | A1 | 10/2007 | Marchand et al. |
| 2007/0239265 | A1 | 10/2007 | Birdsall |
| 2007/0239266 | A1 | 10/2007 | Birdsall |
| 2007/0239269 | A1 | 10/2007 | Dolan et al. |
| 2007/0239271 | A1 | 10/2007 | Nguyen |
| 2007/0239273 | A1 | 10/2007 | Allen |
| 2007/0244544 | A1 | 10/2007 | Birdsall et al. |
| 2007/0244545 | A1 | 10/2007 | Birdsall et al. |
| 2007/0244546 | A1 | 10/2007 | Francis |
| 2007/0244553 | A1 | 10/2007 | Rafiee et al. |
| 2007/0244554 | A1 | 10/2007 | Rafiee et al. |
| 2007/0244555 | A1 | 10/2007 | Rafiee et al. |
| 2007/0244556 | A1 | 10/2007 | Rafiee et al. |
| 2007/0244557 | A1 | 10/2007 | Rafiee et al. |
| 2007/0250160 | A1 | 10/2007 | Rafiee |
| 2007/0255394 | A1 | 11/2007 | Ryan |
| 2007/0255396 | A1 | 11/2007 | Douk et al. |
| 2007/0288000 | A1 | 12/2007 | Bonan |
| 2008/0004696 | A1 | 1/2008 | Vesely |
| 2008/0009940 | A1 | 1/2008 | Cribier |
| 2008/0015671 | A1 | 1/2008 | Bonhoeffer |
| 2008/0021552 | A1 | 1/2008 | Gabbay |
| 2008/0048656 | A1 | 2/2008 | Tan |
| 2008/0065011 | A1 | 3/2008 | Marchand et al. |
| 2008/0065206 | A1 | 3/2008 | Liddicoat |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0077234 | A1 | 3/2008 | Styrc |
| 2008/0082165 | A1 | 4/2008 | Wilson et al. |
| 2008/0082166 | A1* | 4/2008 | Styrc ............ A61F 2/2418 623/2.18 |
| 2008/0133003 | A1 | 6/2008 | Seguin et al. |
| 2008/0140189 | A1 | 6/2008 | Nguyen et al. |
| 2008/0147105 | A1 | 6/2008 | Wilson et al. |
| 2008/0147180 | A1 | 6/2008 | Ghione et al. |
| 2008/0147181 | A1 | 6/2008 | Ghione et al. |
| 2008/0147182 | A1 | 6/2008 | Righini et al. |
| 2008/0154355 | A1 | 6/2008 | Benichow et al. |
| 2008/0154356 | A1 | 6/2008 | Obermiller et al. |
| 2008/0161910 | A1 | 7/2008 | Revuelta et al. |
| 2008/0161911 | A1 | 7/2008 | Revuelta et al. |
| 2008/0183273 | A1 | 7/2008 | Mesana et al. |
| 2008/0188928 | A1 | 8/2008 | Salahieh et al. |
| 2008/0215143 | A1 | 9/2008 | Seguin et al. |
| 2008/0215144 | A1 | 9/2008 | Ryan et al. |
| 2008/0228254 | A1 | 9/2008 | Ryan |
| 2008/0228263 | A1 | 9/2008 | Ryan |
| 2008/0234797 | A1 | 9/2008 | Styrc |
| 2008/0234814 | A1* | 9/2008 | Salahieh et al. ............ 623/2.11 |
| 2008/0243246 | A1 | 10/2008 | Ryan et al. |
| 2008/0255651 | A1 | 10/2008 | Dwork |
| 2008/0255660 | A1 | 10/2008 | Guyenot et al. |
| 2008/0255661 | A1 | 10/2008 | Straubinger et al. |
| 2008/0262593 | A1 | 10/2008 | Ryan et al. |
| 2008/0269878 | A1 | 10/2008 | Iobbi |
| 2008/0300678 | A1* | 12/2008 | Eidenschink et al. ....... 623/2.18 |
| 2009/0005863 | A1 | 1/2009 | Goetz et al. |
| 2009/0012600 | A1 | 1/2009 | Styrc et al. |
| 2009/0048656 | A1 | 2/2009 | Wen |
| 2009/0054976 | A1 | 2/2009 | Tuval et al. |
| 2009/0069886 | A1 | 3/2009 | Suri et al. |
| 2009/0069887 | A1 | 3/2009 | Righini et al. |
| 2009/0069889 | A1 | 3/2009 | Suri et al. |
| 2009/0082858 | A1 | 3/2009 | Nugent et al. |
| 2009/0085900 | A1 | 4/2009 | Weiner |
| 2009/0099653 | A1 | 4/2009 | Suri et al. |
| 2009/0138079 | A1 | 5/2009 | Tuval et al. |
| 2009/0164004 | A1 | 6/2009 | Cohn |
| 2009/0164006 | A1 | 6/2009 | Seguin et al. |
| 2009/0171447 | A1 | 7/2009 | VonSegesser et al. |
| 2009/0192585 | A1 | 7/2009 | Bloom et al. |
| 2009/0192586 | A1* | 7/2009 | Tabor et al. .................. 623/1.11 |
| 2009/0192591 | A1 | 7/2009 | Ryan et al. |
| 2009/0198316 | A1 | 8/2009 | Laske et al. |
| 2009/0216310 | A1 | 8/2009 | Straubinger et al. |
| 2009/0216312 | A1 | 8/2009 | Straubinger et al. |
| 2009/0216313 | A1 | 8/2009 | Straubinger et al. |
| 2009/0222082 | A1 | 9/2009 | Lock et al. |
| 2009/0234443 | A1 | 9/2009 | Ottma et al. |
| 2009/0240264 | A1 | 9/2009 | Tuval et al. |
| 2009/0240320 | A1 | 9/2009 | Tuval |
| 2009/0259290 | A1* | 10/2009 | Bruszewski ............ A61F 2/07 623/1.13 |
| 2009/0270971 | A1* | 10/2009 | Xiao et al. .................... 623/1.14 |
| 2009/0287296 | A1 | 11/2009 | Manasse |
| 2010/0004740 | A1 | 1/2010 | Seguin et al. |
| 2010/0030328 | A1 | 2/2010 | Seguin et al. |
| 2010/0036479 | A1 | 2/2010 | Hill et al. |
| 2010/0036485 | A1 | 2/2010 | Seguin |
| 2010/0069852 | A1 | 3/2010 | Kelley |
| 2010/0094411 | A1 | 4/2010 | Tuval et al. |
| 2010/0100167 | A1 | 4/2010 | Bortlein et al. |
| 2010/0131054 | A1 | 5/2010 | Tuval et al. |
| 2010/0137979 | A1 | 6/2010 | Tuval et al. |
| 2010/0145439 | A1 | 6/2010 | Seguin et al. |
| 2010/0152840 | A1 | 6/2010 | Seguin et al. |

(56) References Cited

U.S. PATENT DOCUMENTS

| | | | |
|---|---|---|---|
| 2010/0161045 A1 | 6/2010 | Righini | |
| 2010/0198346 A1 | 8/2010 | Keogh et al. | |
| 2010/0234940 A1 | 9/2010 | Dolan | |
| 2010/0256723 A1 | 10/2010 | Murray | |
| 2010/0274187 A1* | 10/2010 | Argentine | A61F 2/95 604/96.01 |
| 2013/0073026 A1* | 3/2013 | Russo | A61F 2/852 623/1.12 |
| 2013/0297001 A1* | 11/2013 | Kasprzak | A61F 2/966 612/1.12 |
| 2014/0288639 A1* | 9/2014 | Gainor | A61F 2/2427 623/2.11 |
| 2014/0296975 A1* | 10/2014 | Tegels | A61F 2/2418 623/2.18 |
| 2014/0358224 A1* | 12/2014 | Tegels | A61F 2/2418 623/2.14 |
| 2015/0005874 A1* | 1/2015 | Vidlund | A61F 2/2418 623/2.14 |
| 2015/0142103 A1* | 5/2015 | Vidlund | A61F 2/2418 623/2.17 |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1 000 590 | 5/2000 |
| EP | 1057460 A1 | 6/2000 |
| EP | 1255510 | 11/2002 |
| EP | 0 937 439 | 9/2003 |
| EP | 1 600 121 | 11/2005 |
| EP | 1469797 | 11/2005 |
| EP | 2257242 | 12/2010 |
| FR | 2788217 | 12/1999 |
| FR | 2815844 | 5/2000 |
| FR | 2906454 | 4/2008 |
| GB | 2056023 | 3/1981 |
| GB | 2433700 | 12/2007 |
| SU | 1271508 | 11/1986 |
| WO | 95/29640 | 11/1995 |
| WO | 98/36790 | 9/1998 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | WO2005/046526 | 5/2005 |
| WO | 2006/026371 | 3/2006 |
| WO | WO2007/071436 | 6/2007 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |
| WO | 2010/104638 | 9/2010 |
| WO | 2010/141626 | 12/2010 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

(56) References Cited

OTHER PUBLICATIONS

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" , Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

\* cited by examiner

TRANSCATHETER VALVE STRUCTURE AND METHODS FOR VALVE DELIVERY

TECHNICAL FIELD

The present invention relates to the implantation of transcatheter valves. More particularly, it relates to transcatheter valve structures, delivery systems, and methods of percutaneously implanting prosthetic heart valves.

BACKGROUND

Diseased or otherwise deficient heart valves can be repaired or replaced using a variety of different types of heart valve surgeries. One general type of heart valve surgery involves an open-heart surgical procedure that is conducted under general anesthesia, during which the heart is stopped and blood flow is controlled by a heart-lung bypass machine. This type of valve surgery is highly invasive and exposes the patient to a number of potential risks, such as infection, stroke, renal failure, and adverse effects associated with use of the heart-lung machine, for example.

Due to the drawbacks of open-heart surgical procedures, there has been an increased interest in minimally invasive and percutaneous replacement of cardiac valves. Such surgical techniques involve making a relatively small opening in the skin of the patient, thereby providing access to the vascular system. A valve assembly may then be inserted into the patient and delivered to the heart via a delivery device similar to a catheter. This technique is often preferable to more invasive forms of surgery, such as the open-heart surgical procedure described above.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures. These leaflet-like structures can be used with heart valve bioprostheses, which involves using a natural valve material (e.g., a porcine valve) to make a heart valve. More specifically, these bioprosthetic replacement valves include a valved segment that is mounted in some manner within an expandable stent or frame structure to make a valved stent. In order to prepare such a valve for percutaneous implantation, one type of valved stent can be initially provided in an expanded or uncrimped condition, then crimped or compressed around a balloon portion of a catheter until it is as close to the diameter of the catheter as possible. When it is desired to expand the stent, such as when the stent is at its desired implantation location, the balloon is inflated to provide a certain outward radial force to achieve a particular stent expansion. In other percutaneous implantation systems, the stent of the valved stent can be made of a self-expanding material. With these systems, the valved stent is crimped down to a desired size and held in that compressed state within a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

Although there have been advances in percutaneous valve replacement techniques and devices, there is a continued desire to provide different stent or frame structures and delivery systems for delivering cardiac valves to an implantation site in a minimally invasive and percutaneous manner. There is also a continued desire to be able to control the inflow side of a valve during the implantation process to control the accuracy of placement within the body.

SUMMARY

In one aspect of the invention, a delivery system is provided that can be used in a number of areas of a patient's anatomy, with one particular exemplary placement involving transfemoral delivery of a new or replacement aortic valve to the native aortic valve area of a patient. With the present invention, the physician can more clearly determine the final location of a valve before it is completely deployed within a patient. In this way, the location of the valve can be adjusted to optimize valve placement within the patient.

It is noted that in the implantation of devices using other available systems, once an implantable device is attached to a delivery catheter, it can sometimes be difficult to detach it from the catheter without leaving behind any components that are not necessary for the functioning of the implanted device. In contrast, the implantable devices of the invention overcome this issue by using an invertible structure that is attached to the inflow circumference of the replacement valve. The invertible structure provides for secure attachment to the delivery system, easy detachment from the delivery system with certain manipulation of the delivery system and stent, and also extra structural integrity to the implanted valve or device once it has been deployed. In addition, the devices of the invention include an edge that can be controlled by attaching it directly to the delivery catheter (e.g., the inflow edge of the device).

In one aspect of the invention, when an implantable device or valve is loaded onto a catheter or delivery system, an invertible structure of the device is located closest to the distal tip of the delivery system and the valve and its scaffold, frame, or stent are located proximal to the invertible structure. At this point, the invertible structure can be considered to be in an inverted state. When the device is deployed, the invertible structure moves to a state in which it is no longer inverted, and is instead located or positioned inside the valve scaffold. In this way, it can provide additional radial force and better skirt apposition for the deployed valve.

In one aspect of the invention, an invertible structure is attached to the inflow end of an endoluminally delivered heart valve, although it is understood that it can also be used with other devices that are delivered using endoluminal and/or transcatheter delivery methods. At least a portion of the invertible structure can be considered to be inverted relative to the valve and then attached to the tip of a catheter or other delivery system structure, such as with a sprocket or spindle mechanism. The inflow end of the valve is held down in the tip area of the catheter, thereby allowing the device to be accurately positioned within the heart. The invertible structure can then be slowly deployed, which allows for complete apposition of the heart valve structure before being released. When released, the invertible structure will revert to a non-inverted position in which it will rest against or within the valve structure. One advantage of this additional structure is that it provides a portion of the stent that has an additional layer, which can allow the overall structure to provide additional radial force to the surrounding organ in which it is implanted.

In another aspect of the invention, an invertible structure is attached to one end of a stented transcatheter heart valve in such a way that it provides additional length to the stented valve during the delivery and deployment processes, yet the overall length of the stented valve does not increase after it is deployed. This is due to the fact that the invertible structure rotates or flips to be adjacent to the stent structure after it is deployed such that it does not increase the overall length of the structure.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
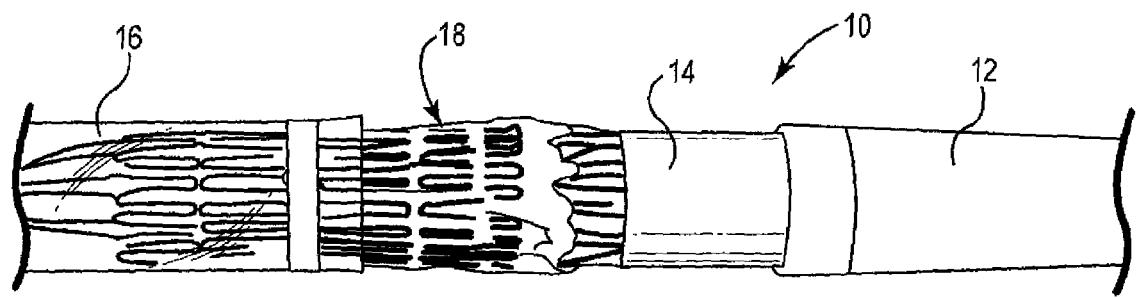
FIG. 1 is a front view of a delivery system with an attached stent or frame structure in accordance with the invention, with a sheath of the delivery system partially retracted relative to the stent.

As referred to herein, the prosthetic heart valves used in accordance with the various devices and methods may include a wide variety of different configurations, such as a prosthetic heart valve having tissue leaflets or a synthetic heart valve having polymeric, metallic, or tissue-engineered leaflets, and can be specifically configured for replacing any heart valve. Further, while portions of the description herein refer to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example. The present invention is not limited in use to heart valve replacement devices and systems, however, but can be used for a wide variety of vascular devices and systems, such as can be used with stent grafts, stents, vena cava filters, occluders, and the like.

In general, one embodiment of the stents or stent frames described herein includes support structures that comprise a number of strut or wire portions arranged relative to each other to provide a desired compressibility and strength to the heart valve. Other details on particular features of the stents or stent frames used in accordance with the invention are also described below; however, in general terms, the stents or stent frames described herein are generally tubular support structures having an internal area in which leaflets are secured. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided as independent structures from each other (e.g., bovine or equine pericardial leaflets) and subsequently assembled to the support structure of the stent frame to provide a valve structure. In another alternative, the stent frame and leaflets can be fabricated at the same time, such as may be accomplished using high strength nano-manufactured NiTi films of the type produced at Advanced Bio Prosthetic Surfaces, Ltd. (ABPS) of San Antonio, Tex., for example. The support structures are often configured to accommodate three leaflets, although it is contemplated that replacement prosthetic heart valves of the types described herein can incorporate more or less than three leaflets.

Orientation and positioning of stent frames relative to the delivery systems of the invention may be accomplished either by self-orientation of the stent frames (such as by interference between features of the stent frame and a previously implanted stent frame or valve structure) or by manual orientation of the stent frame to align its features with anatomical or previous bioprosthetic features, such as can be accomplished using fluoroscopic visualization techniques, for example. For example, when aligning the stent frames of the invention with native anatomical structures, they should be aligned so as to not block the coronary arteries, and native mitral or tricuspid valves should be aligned relative to the anterior leaflet and/or the trigones/commissures.

Some embodiments of the stent frames described herein can be a series of wires or wire segments arranged so that they are capable of transitioning from a collapsed state to an expanded state. In some embodiments, a number of individual wires comprising the support structure can be formed of a metal or other material. These wires are arranged in such a way that a support structure allows for folding or compressing to a contracted state in which its internal diameter is smaller than its internal diameter when it is in an expanded state. In its collapsed state, such a support structure with attached valves can be mounted on a delivery system. The support structure is configured so that it can be changed to its expanded state when desired, such as by the relative movement of one or more sheaths relative to the length of the stent frame. The delivery systems used for such stent frames should be provided with degrees of rotational and axial orientation capabilities in order to properly position the stent frame at its desired location.

The wires of the support structure of the stent frames in embodiments of the invention can be formed from a shape memory material such as a nickel titanium alloy (e.g., Nitinol), for one example. With this material, the support structure will be self-expandable from a contracted state to an expanded state, such as by the application of heat, energy, and the like, or by the removal of external forces (e.g., compressive forces). This support structure can also be compressed and re-expanded multiple times without damaging the structure of the stent frame. In addition, the support structure of such an embodiment may be laser cut from a single piece of material or may be assembled from a number of different components. For these types of stent frame structures, one example of a delivery system that can be used includes a catheter with a retractable sheath that covers the stent frame until it is to be deployed, at which point the sheath can be retracted to allow the stent frame to expand. However, it is contemplated that the materials from which the stents are made consist of structures that are expandable with the application of an external force, such as balloon expandable stent structures, for example.

Figure 2:
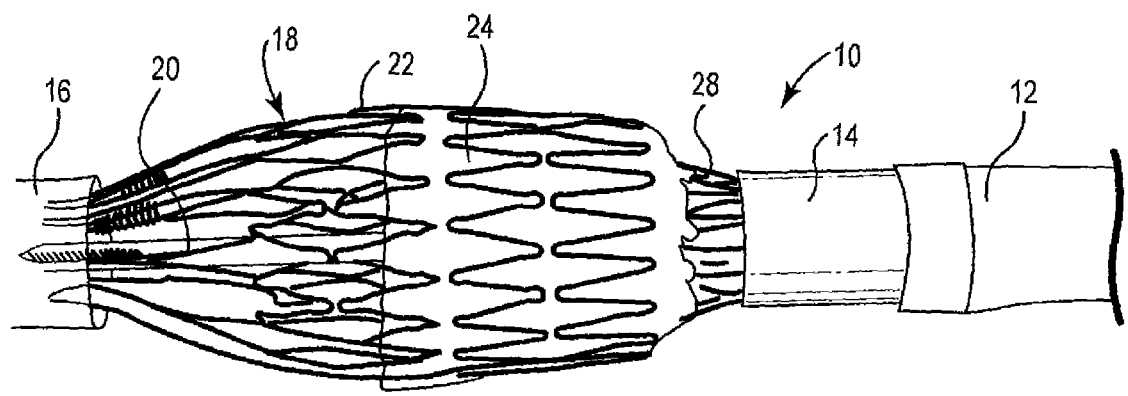
FIG. 2 is a front view of the stent and distal portion of the delivery system of FIG. 1, with the sheath further retracted.

Referring now to the Figures, wherein the components are labeled with like numerals throughout the several Figures, and initially to FIGS. 1 and 2, the distal end of one embodiment of a stent delivery system 10 is illustrated. Delivery system 10 includes a distal tip 12 from which a central longitudinal shaft 20 extends, a capturing collar 14, and a sheath 16. As shown in FIG. 1, a valved stent 18 is compressed and loaded onto the delivery system 10, and the sheath 16 is partially withdrawn in a proximal direction (i.e., to the left, in this figure) relative to the distal tip 12. It is noted that when this delivery system 10 is initially being introduced to deliver the valved stent 18 to a desired implantation location, the sheath 16 can be located close enough to the distal tip 12 that it covers all or most of the valved stent 18. The sheath 16 can optionally be positioned to also cover or partially cover the capturing collar 14 so that it protects more of the delivery system during the insertion process, such as by positioning the distal end of the sheath 16 adjacent to the proximal end of the distal tip 12. The sheath 16 can be positioned in this way during the process of delivering the stent to a location within the patient and until the valved stent 18 is properly located within the patient's anatomy. Thus, the configuration of the components of the delivery system 10 relative to the stent 18 shown in FIG. 1 represents one embodiment of the situation immediately after the valved stent 18 is in its desired location and the process of releasing the stent by retracting the sheath 16 has just started, and FIG. 2 represents one embodiment of the condition of the stent 18 as the sheath 16 is further retracted from the stent.

The valved stent 18 generally comprises a stent frame 22 with a valve attached within its internal area, where the figures illustrate a representative tissue or valve material 24, which illustrates an exemplary volume of material that can be used for a valve and sealing skirt. The valve can be made of any of a number of materials and can be configured in a number of different ways, such as by using the materials and/or configurations described above to manufacture prosthetic valves, or as made using other techniques and materials. As shown in this embodiment, the portion of the stent frame 22 in which the valve is located includes a wire structure arranged as rows of relatively sinusoidal or zigzag shapes positioned adjacent to each other. In particular, the "peaks" of one row of wire structure are arranged to meet the "valleys" of an adjacent row of wire structure. The valve can be located at any desired position along the length of the stent that will coincide with a desired location of the valve within the patient's anatomy.

Once the valved stent 18 is in its approximate desired position within the patient, the sheath 16 is pulled away from the distal tip 12 (i.e., in a proximal direction), as is illustrated in FIG. 2, to unsheath the distal end of the stent 18. The material used for the stent 18 in this embodiment is a shape-memory material, such that removal of the compressive force provided by the sheath 16 will allow the stent 18 to diametrically expand relative to the shaft 20 adjacent to its distal end. However, the proximal end of the stent frame will still be contained in its compressed state within the sheath 16 at this point in the stent frame delivery process. In addition, the distal end of the stent frame 22 is partially constrained from radial expansion by an invertible structure 28 that is attached to a portion of the delivery system, as described below. In this embodiment, the invertible structure 28 is permanently or semi-permanently attached at one end to the sealing skirt by sutures and temporarily attached to a structure of the delivery system on the other end. The invertible structure 28 generally comprises a ring of material that is arranged in a sinusoidal or zigzag shape around its circumference. The peaks and valleys of the structure 28 around its circumference may have the same or different sizes, shapes, and the like as other peaks and valleys of that structure. A first end of the structure 28 is partially constrained within the inner diameter of the capturing collar 14, while a second end of the structure 28 is attached to the valved stent 18 via sutures. It is noted that the term "invertible structure" is used herein to describe the portion of the stent that is generally configured to be an extension from one end of the stent and that can rotate, turn, or flip about that end of the stent to extend generally along a portion of that stent. Alternatively, this structure may be referred to as "eversible," or capable of turning inside out relative to the structure of the stent.

Figure 3:
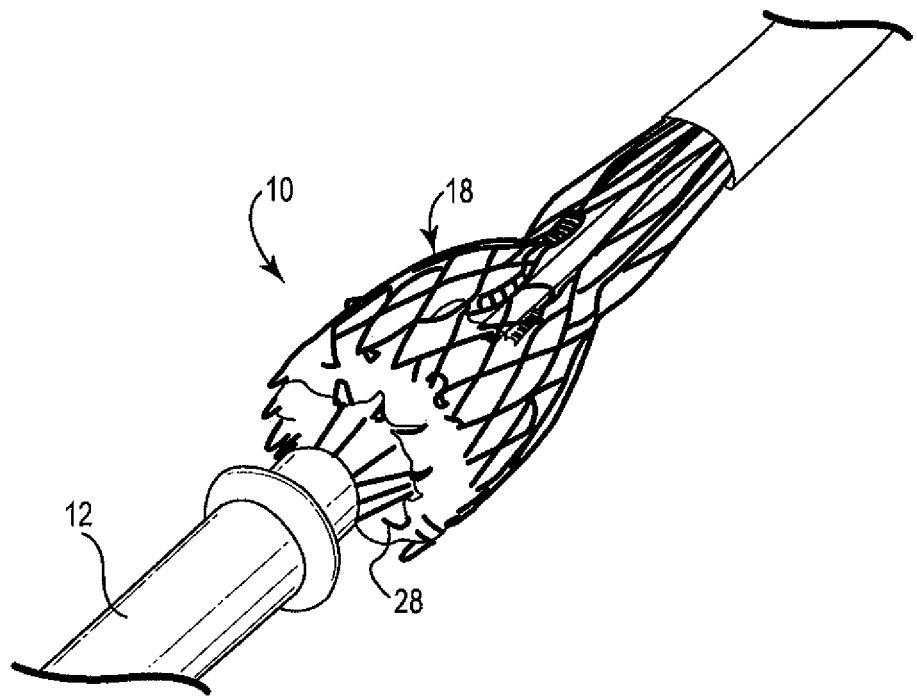
FIG. 3 is a perspective view of the stent and distal portion of the delivery system of FIGS. 1 and 2, showing a capture mechanism or invertible structure of the system as it is beginning to be released.
Figure 4:
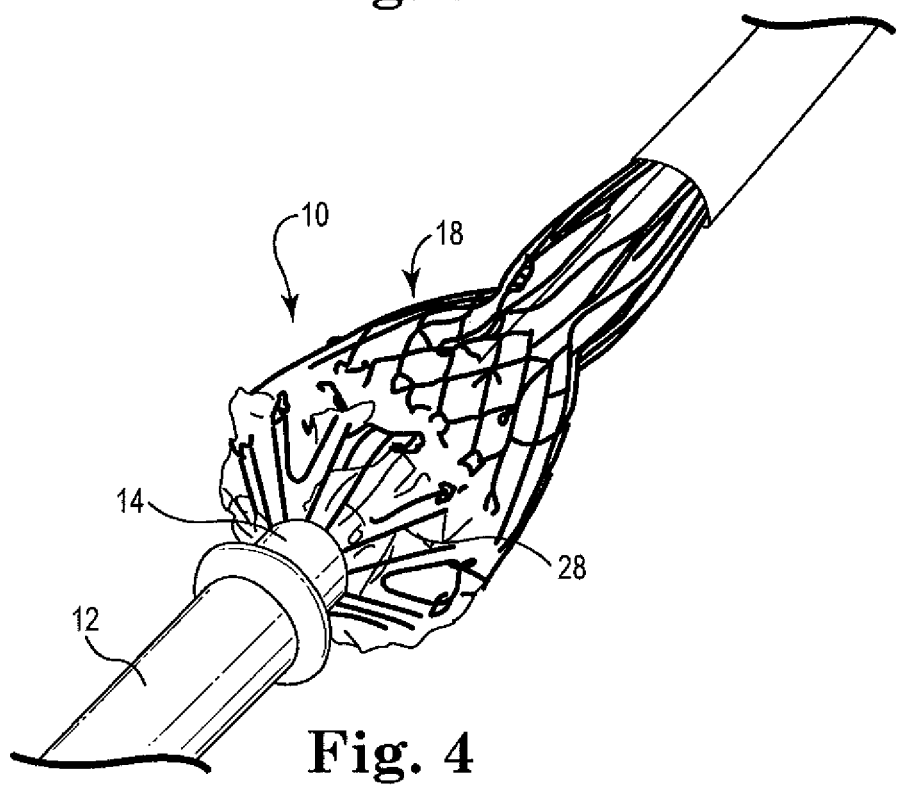
FIG. 4 is a perspective view of the stent and distal portion of the delivery system of FIGS. 1-3, showing the invertible structure in a position in which it is further released from the delivery system.
Figure 5:
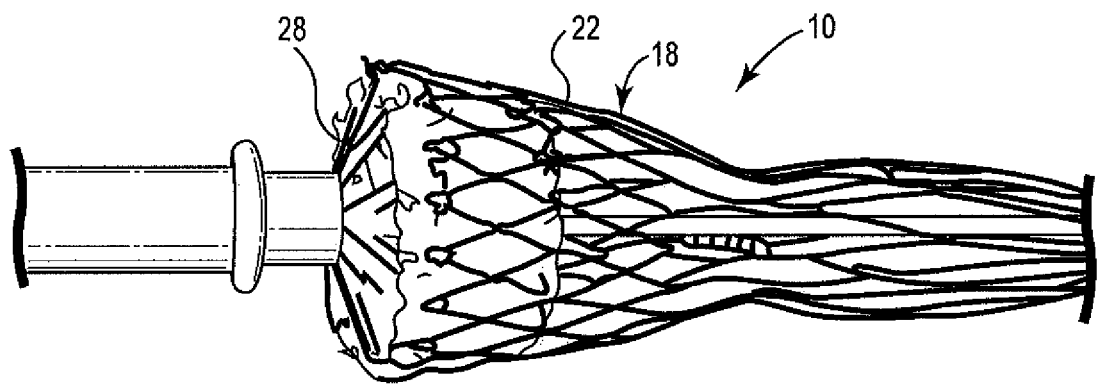
FIG. 5 is a front view of the distal portion of the delivery system and stent of FIGS. 1-4, showing the invertible structure just before it is completely released from the delivery system, wherein the invertible structure is at approximately 90 degrees relative to the longitudinal axis of the delivery system.
Figure 6:
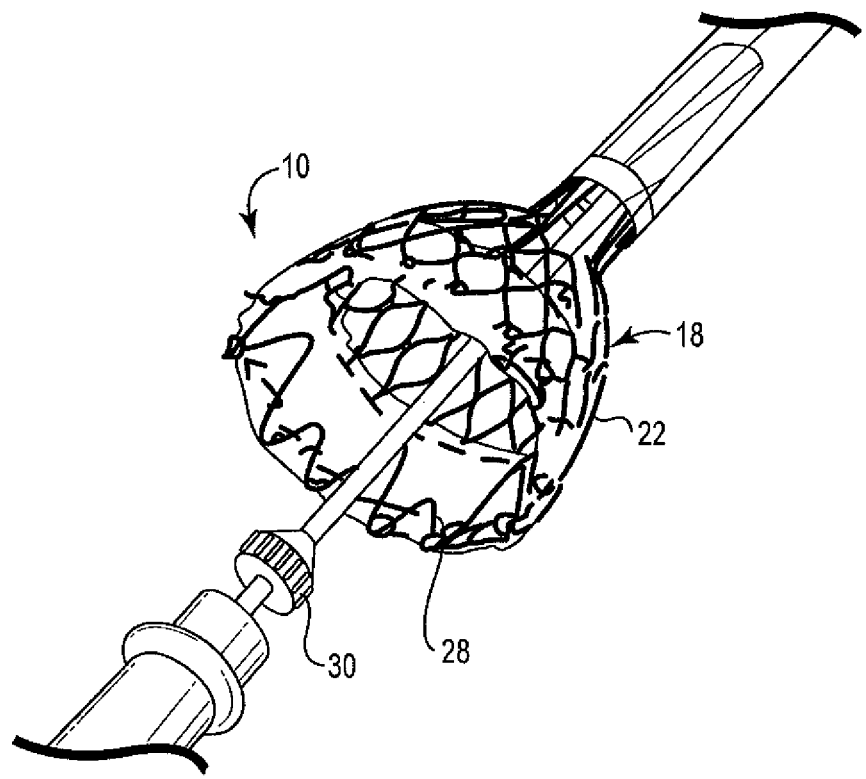
FIG. 6 is a perspective view of the delivery system and stent of FIGS. 1-5, showing the invertible structure in its released position relative to the stent to which it is attached.

Referring now to FIGS. 3-6, one exemplary process of releasing the invertible structure 28 relative to the valved stent 18 and the delivery system 10 is illustrated. To initiate this process, the collar 14 is held stationary while a sprocket type member 30 (see FIG. 6) is retracted. The member 30 is attached to a tube that rides over another tube that is in turn attached to the distal tip 12 and collar 14. In this way, the member 30 can be moved independently relative to the collar 14. In FIG. 3, the invertible structure 28 is just beginning to be released from the capturing collar 14, and it is in its inverted state relative to the stent 18. FIG. 4 illustrates the invertible structure 28 as it is further released from the capturing collar 14. FIG. 5 shows the invertible structure 28 oriented at approximately 90 degrees to the distal end of the stent frame 22, which is the position in which it will be located immediately prior to it being released from the delivery system. Finally, FIG. 6 shows the invertible structure 28 after it is released from the delivery system 10, but before the delivery system is removed from the area of the stent. After this release, the invertible structure 28 is oriented in its opposite or non-inverted position, where it is positioned within the distal end of the stent frame 22. This structure 28 provides additional structural integrity to the distal end of the stent frame 22 due to the "dual layer" type of structure in this area.

It is further noted that the delivery system 10 includes sprocket-type member 30, as mentioned above, which is visible in FIG. 6. This member 30 is used for loading and holding the invertible structure 28 during delivery of the stent 18 and is also used for controllably releasing the stent 18 from the delivery system 10. In this embodiment, the V-shaped structures of the stent can be placed over the extending portions of the member 30 so that when the stent is compressed, the stent can be contained between the member 30 and the collar 14. It is understood, however, that other methods and devices can be used to maintain the invertible structure in its desired pre-release condition until it desired to release the stent from the delivery system.

Although much of the discussion herein is directed to heart valves that are compressible and expandable for use in transcatheter valve delivery operations, the heart valve structures of the invention can also be used with more invasive forms of surgery, such as open-heart surgery. In such cases, the stent structure is not necessarily compressible and expandable, but may still include an invertible structure at one or both ends that provides a second stent layer that is adjacent to the stent frame. This layer can provide extra structural integrity to the stent, for example.

It is further noted that the invertible structure may be made of one or more materials that are the same or different from one or more materials from which the stent is made. Also, in order to provide a final structure with certain desired performance characteristics (e.g., flexibility, strength, and the like), an invertible structure may be made of the same material as the stent to which it is attached, but the thickness, shape, or other material properties may be different between the invertible structure and the stent.

Figure 7:
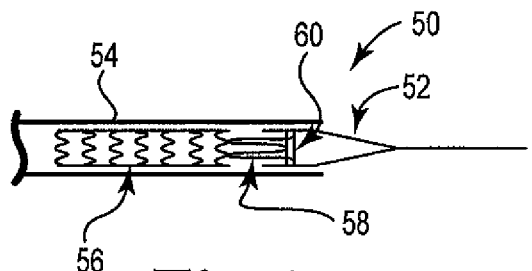
FIG. 7 is a schematic front view of a stent and distal portion of a delivery system, with the stent in its compressed condition.

FIGS. 7-12 schematically illustrate an embodiment of the invention that is similar to that discussed above relative to FIGS. 1-6. In particular, these figures illustrate a distal end of a delivery system 50 that includes a distal tip 52, a spindle 60 (e.g., a sprocket-type member), and a sheath 54. As shown in FIG. 7, a stented transcatheter valve 56 (which includes a stent frame with a valve attached within its interior area) is compressed and loaded onto the delivery system 50, and the sheath 54 is used to compress and cover the valve 56. An invertible structure 58 extends from the distal end of the valve 56 and toward the distal end 52 of the delivery system, and this invertible structure 58 is also held within the sheath 54. A spindle or other holding mechanism 60 holds the invertible structure 58 relative to the distal tip 52, and the spindle 60 is located within a capturing collar 62 at this point in the delivery process.

Figure 8:
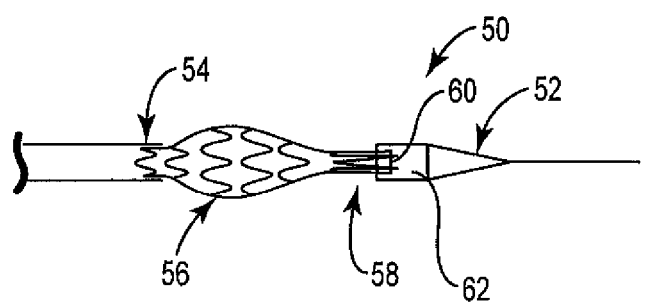
FIG. 8 is a schematic front view of the delivery system and stent of FIG. 7, with the stent in a partially deployed condition.

Once the valve 56 is in its approximate desired position, the sheath 54 is pulled away from the distal tip 52 (i.e., in a proximal direction), as is illustrated in FIG. 8, until the distal end of the valve 56 is unsheathed. When the material used for the stent of the valve 56 in this embodiment is a shape-memory material, removal of the compressive force provided by the sheath 54 will allow the valve 56 to diametrically expand. However, a proximal end of the valve 56 can still be contained in its compressed state within the sheath 54 at this point in the valve delivery process. In addition, the distal end of the valve is at least partially constrained from radial expansion by an invertible structure 58, which is attached to a sealing skirt (optional) with a suture or any other configuration that does not restrict the ability of the invertible structure 58 to flip or rotate relative to the stent. The invertible structure 58 may comprise a ring of material that is arranged in a sinusoidal or zigzag shape around its circumference. The peaks and valleys of the structure 58 around its circumference may have the same or different sizes, shapes, and the like as other peaks and valleys of the structure. A first end of the structure 58 is partially constrained within the inner diameter of the capturing collar 62 via the spindle or holding mechanism 60, while a second end of the structure 58 is attached to the valve 56.

Figure 9:
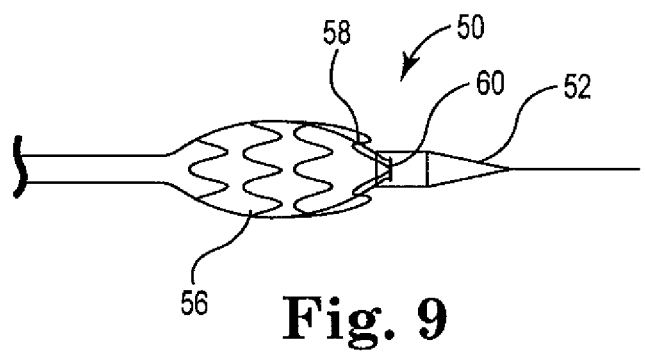
FIG. 9 is a schematic front view of the delivery system and stent of FIGS. 7 and 8, with the stent in a further deployed condition.
Figure 10:
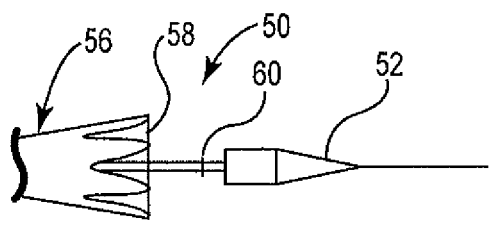
FIG. 10 is a schematic front view of the delivery system and stent of FIGS. 7-9, with the stent in its fully deployed condition.
Figure 11:
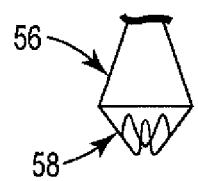
FIG. 11 is a schematic front view of a portion of a stent and attached invertible structure, in accordance with the invention.
Figure 12:
FIG. 12 is a schematic front view of the stent and invertible structure of FIG. 11, with the invertible structure in a non-inverted position relative to the stent structure.

Referring now to FIGS. 9 and 10, the release of the invertible structure 58 relative to the valve 56 and the delivery system 50 is illustrated. In particular, FIG. 9 shows the invertible structure 58 as it is in the process of being released from the capturing collar 62. The invertible structure 58 is in its inverted state relative to the valve 56. FIG. 10 illustrates the invertible structure 58 after it is released from the delivery system 50. After this release, the invertible structure 58 will reorient to its non-inverted position, where it is positioned within the distal end of the valve 56. This structure 58 will provide additional structural integrity to the distal end of the valve 56. FIGS. 11 and 12 illustrate additional views of the invertible structure 58 in its inverted and non-inverted positions relative to the distal end of the valve 56, respectively.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A valved stent comprising:
   a stent structure comprising a generally tubular body portion, an interior area, a first end, and a second end;
   a valve comprising a plurality of leaflets and attached to the stent structure and disposed entirely within the interior area of the stent structure in a delivery configuration; and
   an invertible structure having a first end coupled to the stent structure such that the invertible structure extends from the stent structure in the delivery configuration,
   wherein the invertible structure is pivotable relative to the stent structure from the delivery configuration to an implanted configuration,
   wherein the invertible structure extends beyond the stent structure in the delivery configuration, and
   wherein the invertible structure folds inwardly towards the interior area of the stent structure and is positioned directly adjacent to an interior wall of the stent structure in the implanted configuration.

2. The valved stent of claim 1, wherein the invertible structure is pivotable relative to the first end of the stent structure, and
   wherein the valve is positioned adjacent to the invertible structure.

3. The valved stent of claim 1, wherein the invertible structure further comprises a third configuration between the delivery configuration and implanted configuration, wherein the invertible structure is generally perpendicular to the stent structure when in the third configuration.

4. The valved stent of claim 1, further comprising at least one intermediate invertible structure pivotably attached to the stent structure within the interior area and between the first and second ends.

5. The valved stent of claim 1, further comprising a sealing skirt extending around at least a portion of the circumference of the tubular body at one of the first and second ends of the stent structure.

6. The valved stent of claim 1, wherein a length of the invertible structure is less than a length of the stent structure.

7. The valved stent of claim 1, wherein the invertible structure comprises at least one wire having multiple peaks and valleys positioned around a circumference of one of the first and second ends of the stent structure.

8. The valved stent of claim 1, wherein the invertible structure provides outward radial force against the interior area of the stent structure when the invertible structure is in the implanted configuration.

9. The valved stent of claim 1, wherein at least one of the stent structure and invertible structure comprise a shape memory material.

10. The valved stent of claim 1, wherein a second end of the invertible structure is configured to attach to a delivery system.

11. The valved stent of claim 1, further comprising an intermediate material attached to the stent structure, wherein the first end of the invertible structure is attached to the intermediate material.

\* \* \* \* \*